United States Patent
Bequet-Sharber et al.

[11] Patent Number: 5,944,675
[45] Date of Patent: Aug. 31, 1999

[54] CAST REMOVAL AID

[75] Inventors: Robin Bequet-Sharber; Michael A. Schmieder, both of Flagstaff, Ariz.; Kirk L. Sheffield, Draper, Utah

[73] Assignee: Gore Enterprise Holdings, Inc., Newark, Del.

[21] Appl. No.: 08/786,359

[22] Filed: Jan. 16, 1997

Related U.S. Application Data

[60] Provisional application No. 60/010,263, Jan. 19, 1996.

[51] Int. Cl.$^6$ ........................................ A61F 15/02
[52] U.S. Cl. .................................................. 602/9
[58] Field of Search ............................ 602/8–10

[56] References Cited

U.S. PATENT DOCUMENTS 3,495,590  2/1970  Zeiller .
3,985,129  10/1976  Huene .
5,474,634  12/1995  Termanini ................. 156/250

FOREIGN PATENT DOCUMENTS 0289681  9/1988  European Pat. Off. .
93/10732  10/1993  WIPO .

*Primary Examiner*—Richard J. Apley
*Assistant Examiner*—Kim M. Lee
*Attorney, Agent, or Firm*—David J. Johns

[57] ABSTRACT

The present invention is an improved device to aid in the safe removal of casts from a patient. Even with the advent of safe cast removal tools, such as oscillating saws, there remains a distinct risk that a patient's skin will be cut or burned during cast removal. The present invention provides a protective shield that is mounted between the outer shell of a cast and a patient's skin to protect against cut-through and burning of the patient. The preferred protective shield comprises a woven expanded polytetrafluoroethylene fabric that has proven to be highly effective at avoiding cut-through by oscillating saws and the like.

13 Claims, 4 Drawing Sheets

CAST REMOVAL AID

RELATED APPLICATIONS

The present application is a regular application based upon United States Provisional Patent Application No. 60/010,263 filed Jan. 19, 1996.

BACKGROUND OF THE INVENTION

1. Field of the Invention

The present invention relates to devices used to aid in the removal of casts.

2. Description of Related Art

Casts normally comprise a hard outer shell (usually made of fiberglass or plaster) and soft, cushy cast padding (such as gauze, pre-formed cast padding, and/or a stockinet) beneath it. The purpose of the hard outer shell is to immobilize and protect the body part being the cast. The purpose of cast padding is two-fold. First, it provides a comfortable interface between the outer shell and the patient's skin. Second, it provides protection from a cast saw during cast removal.

The typical cast saw uses an oscillating blade designed to cut through hard substances while causing little damage to pliable materials that move with the oscillating saw blade, such as cast padding or a patient's skin. While oscillating blades work relatively well in most cast removal applications, periodically more pressure is applied than necessary with the cast saw and the blade penetrates the cast padding, cutting or burning the patient's skin below. In addition, some cast padding shift with the cast saw blade more readily than others. Those that tend not to shift are less forgiving of additional pressure applied during cast removal. Finally, there are particular casting applications, such as in so-called direct or total contact casting, where a patient's skin is particularly vulnerable. Where a cast is applied with little or no cast padding, the risk of cutting or burning the patient has proven to be significant.

Currently, there are a variety of products utilized in an attempt to avoid cutting or burning the patient during cast removal. A common approach is to use a long, flat, thin plastic or metal devices that is inserted beneath the cast at the time of cast removal. One such device is commercially available from W. L. Gore & Associates, Inc., Flagstaff Ariz., under the trademark ZIP STICK. These devices are designed to protect the skin from the cast saw blade. They are, however, difficult to insert between the skin and the cast. In particular, bony areas like the wrist or ankle are typically so snug that these devices often will not fit in that portion of the cast. In addition, there are places that are inaccessible by these devices due to the length of the cast (for example, long leg casts are generally longer than these devices).

Other approaches to protect a patient's skin from cast removal tools have also been attempted, with little success. For example, it is common to increase the amount of cast padding under the outer shell to provide better buffer from poor cutting techniques. Additionally, subsequent to the present invention it has been suggested to the present inventors that a strip of hook-and-loop material (such as VELCRO®) may be used within a cast to provide a cutting substratum. Unfortunately, these approaches have been largely unsuccessful. First, these materials provide little or no cut-through resistance when exposed to a cast saw. Accordingly, any additional protection is dependent upon the added materials providing greater distance between the cast saw and the patient's skin. Second, adding additional padding to increase the distance between the cast outer shell and the patient's skin is not a viable option in instances where little to no cast padding is used (e.g., total contact casts).

In light of the foregoing, it is a purpose of the present invention to provide a means for effectively protecting a patient's skin during cast removal.

It is a further purpose of the present invention to provide a means for protecting a patient's skin during cast removal particularly under circumstances where a patient's skin must be more carefully safeguarded, such as where reduced quantities of cast padding are employed.

These and other purposes of the present invention will become evident upon review of the following specification.

SUMMARY OF THE INVENTION

The present invention is a device that aids in the removal of casts. Essentially, the present invention is a cut resistant and heat buffering protective shield (such as a strip or an entire cover) formed directly within the cast during the initial casting procedure. The protective shield allows medical personnel to freely cut through the outer shell of the cast during removal without risk of burning or cutting a patient's skin underneath.

In a preferred embodiment of the present invention, the cast removal aid of the present invention comprises a woven strip of expanded polytetrafluoroethylene (PTFE) fibers. It has been determined that such a strip of expanded PTFE material is particularly effective at resisting cut-through by oscillating cast removal saws, far out performing other strips of materials tested as cast removal aids. By forming the strip of a contrasting color to the other casting materials, the medical personnel are given a clear guide along which to cut to effectuate safe cast removal.

The benefit of the device of the present invention is that it reduces the incidence of cutting and/or burning the patient during cast removal. It is applicable when any cast removal is performed, whether by a cast saw or a heat source (such as a blow dryer), or any other method.

Features of this device include reducing the amount of heat passing through to the patient's skin by absorbing it or deflecting it, and providing increased protection so as to reduce the risk of a blade cutting a patient.

DESCRIPTION OF THE DRAWINGS

The operation of the present invention should become apparent from the following description when considered in conjunction with the accompanying drawings, in which.

DETAILED DESCRIPTION OF THE INVENTION

The present invention is a protective shield that is oriented between a patient's skin and the outside layer of a cast in order to protect the patient's skin from being cut or burned during the process of removing the cast.

Figure 1:
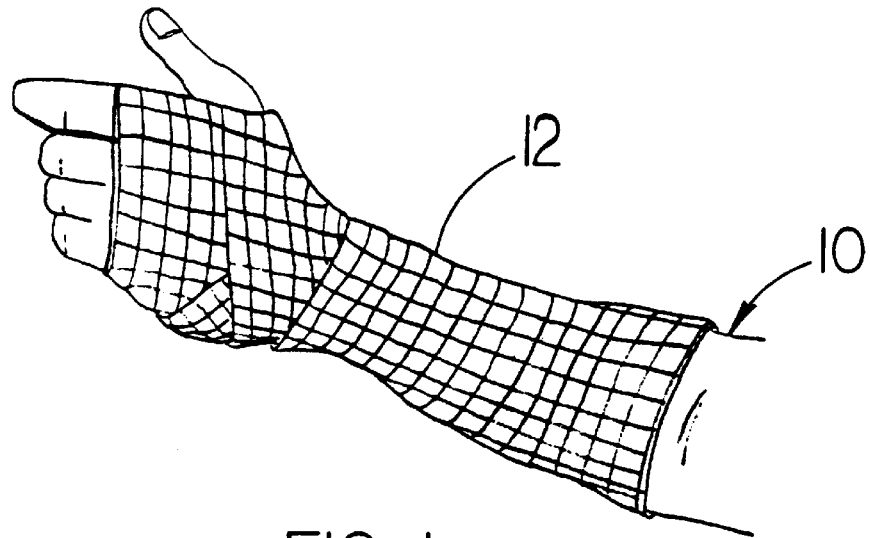
FIGS. 1 through 3 are side elevation views of a patient's arm illustrating the steps of applying a conventional cast and one embodiment of the protective shield of the present invention.

FIG. 1 shows a patient's arm 10 covered with a layer of cast padding 12. In this instance the cast padding is a GORE® Cast Liner padding available from W. L. Gore & Associates, Inc., Flagstaff, Ariz. Gauze, stockinet, and/or other padding layer may be employed with present invention with similar effectiveness.

Figure 3:
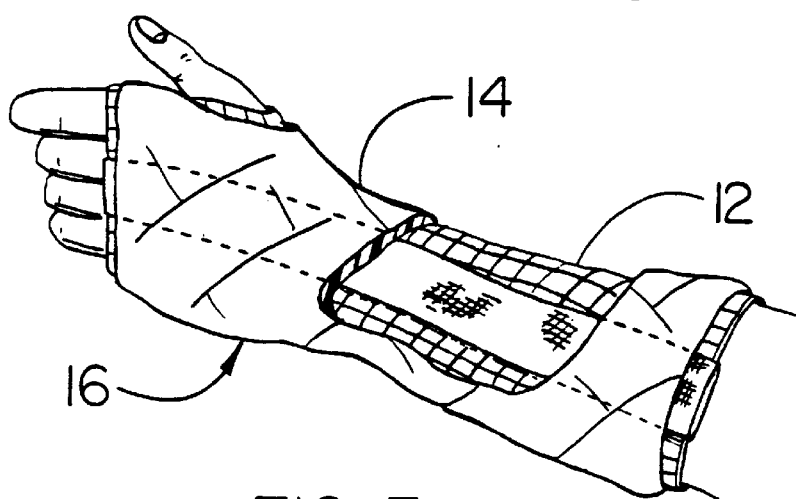

As is shown in FIG. 3, normally following the wrapping of cast padding 12 the padding is then encased in a protective shell 14, such as one made from fiberglass/resin composite or plaster, to form a final cast 16. Unfortunately, to remove such a shell, medical personnel must use cast removal tools (e.g., cutting tools or heat applying tools), which can cause cutting, burning or other injury to the patient.

Figure 2:
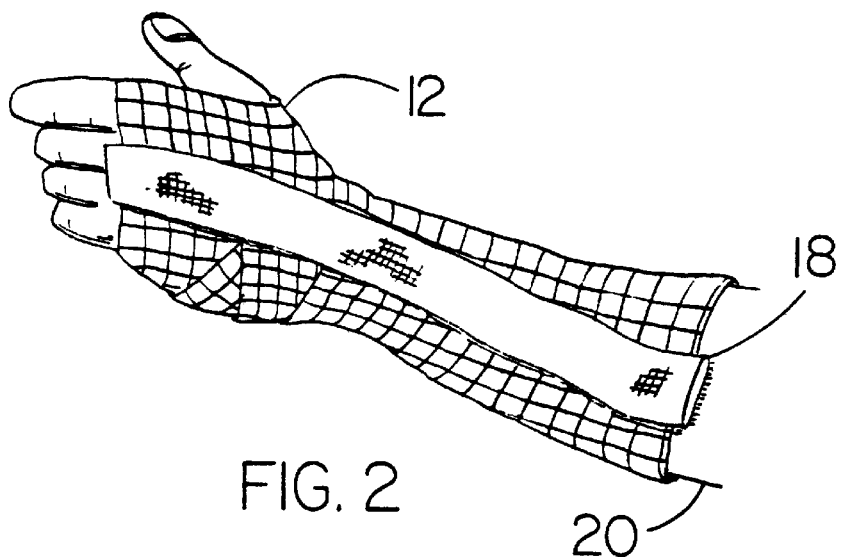

As is shown in FIG. 2, the present invention uses a protective shield 18 positioned within the cast between a patient's skin 20 and the cast removal tool in order to deflect cast removal tool away from the patient's arm and to shield the patient's skin from heat generated by the cast removal tool. The protective shield may comprise one or more strips of material positioned along the length of the cast, such as is shown in FIG. 2, or may comprise a wrap that covers most or all of the area being casted. Once the protective shield 18 is installed, the outer shell can be readily removed by simply operating the cast removal tool over the length of the protective shield 18.

The protective shield 18 of the present invention may comprise a variety of materials that will provide cut through resistance and some degree of heat isolation. As is explained in greater detail below, it has been found that the preferred embodiment of the present invention comprises a weave of expanded polytetrafluoroethylene (PTFE) fibers, such as those produced in accordance with U.S. Pat. No. 3,953,566 to Gore, incorporated by reference. Surprisingly, this material has proven to be highly effective at providing cut through resistance to a typical oscillating cast removal saw, out-performing other materials known for their cut resistance, such as a KEVLAR® aramid fiber available from E. I. duPont de Nemours & Co., Wilmington, Del.

While a fabric made from expanded PTFE is preferred, it should be appreciated that the present invention may employ a variety of materials to achieve the desired properties. Examples of materials that may be employed alone or in combination in the present invention include: PTFE; porous PTFE; expanded PTFE (either porous or non-porous); aramid (such as KEVLAR® aramid fibers); polyester; polypropylene; polyamide; polyethyleneterepthalate (e.g., DACRON® or MYLAR®); fiberglass; etc. While not preferred it may also be possible to construct the present invention using a variety of other materials, such as in combination with the materials listed above. Such materials may include: silk; rubber; spandex (e.g., LYCRA®); cotton; various metals or ceramics, etc.

In choosing a suitable material or materials for use in the present invention, a number of important factors must be considered. First, the material must be resistant to cut through. Second, the material must be fully bio-compatible so as not to risk skin irritation or other condition. Third, if the protective shield is to be used in a cast that will be submerged or otherwise exposed to water, it is important that the protective shield not unduly absorb and retain water (which could lead to bacterial growth and/or cause skin irritation). Other desirable characteristics include low weight and conformability (i.e., the material should be pliable, flexible and supple so as to be adaptable to the unique contours of each casting situation).

Figure 4:
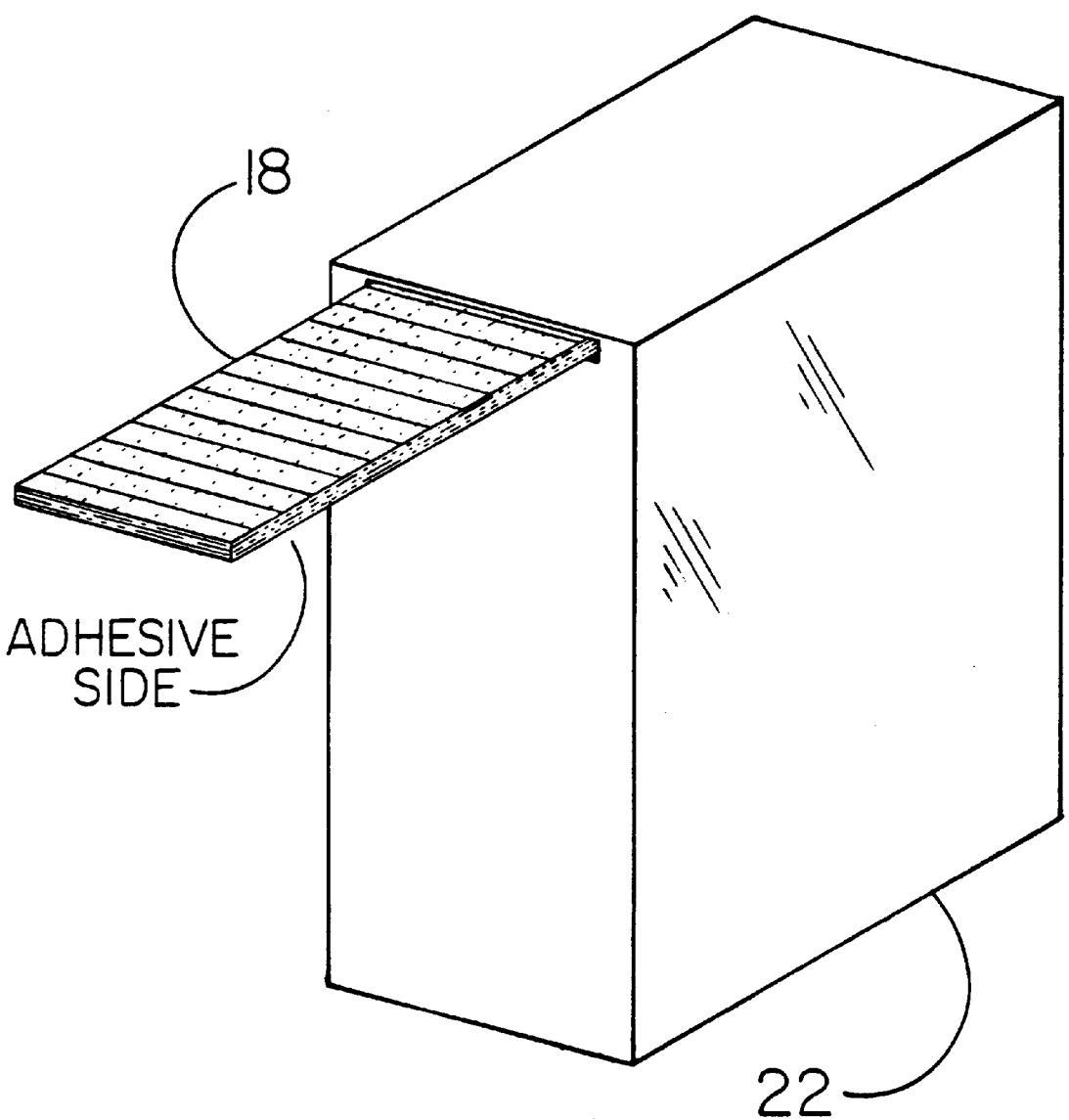
FIG. 4 is a three-quarter isometric view of a roll dispenser dispensing one embodiment of the protective shield of the present invention.

FIG. 4 shows one embodiment of a protective shield 18 of the present invention contained in a dispenser 22. In this instance, the protective shield 18 comprises a strap of material that can be drawn from the dispenser 22 to any desired length and then cut to provide an appropriate strip for mounting within a cast. It should be appreciated that the protective shield 18 may also be provided in pre-cut lengths.

As has been noted, the protective shield 18 of the present invention may be formed as either a strip or a continuous cover. Where a strip is employed, the strip can be mounted in a straight line, as shown in FIG. 2, or as a spiral wrap or in any other manner desired. More than one protective shield may be provided and, where desired, the protective shields may be stacked (e.g., doubled or tripled, etc.) in order to provide added protection.

The preferred protective shield 18 of the present invention comprises a woven material with an adhesive on one side as is described below. As has been noted, the best performing of the protective shields 18 of the present invention that have been tested has proven to be a woven expanded PTFE material. The size of the fiber can vary, but a weight of between about 400 and 1200 denier is generally preferred. The cross sectional geometry of the fiber may be rectangular, oval, circular, or folded.

In the preferred embodiment the protective shield comprises a weave of expanded PTFE fibers. The preferred weave comprises a warp fiber of about 800 to about 1200 denier and a fill fiber of about 400 to about 1200 denier. In an alternate embodiment a 400 denier fiber may be used on the ends of the protective shield to produce a lower profile or tapered edge while 1200 denier is used on the rest of the configuration.

The preferred expanded PTFE fiber comprises a fiber having a denier of about 400 to about 1600, with about 1100 to 1300 denier preferred; a Young's stress-strain modulus of about 75 to about 250 g/denier, with about 150 to about 220 g/denier preferred; an elongation to yield of about 1 to about 5%, with about 2 to 4% preferred; a tenacity at maximum load of about 2 to about 5 g/denier, with about 2 to about 4 g/denier preferred. All such stress-strain properties being measured by conventional methods on an INSTRON tensile strength tester.

The weave should have between about 5 and about 10 twists per inch. The most effective weave tested to date comprises a 1200 denier warp fiber with about 5 twists per inch, and either a 400 or 800 denier fill fiber.

The fiber is woven into a strip. The preferred strip comprises a weave of about 32 pics per inch; a width of about 2 to about 6 cm, and the final thickness of about approximately 1 to 2 mm. The strip will generally comprise about 0.02 pounds of fiber per foot at a 1.25 inch width.

Preferably the protective shield includes means to assist in holding it in place during application. Preferably an adhesive is included on one side of the protective shield, such as a pharmaceutical grade adhesive (e.g., transfer adhesive 1524 available from Minnesota Mining & Manufacturing Co., St. Paul, Minn.).

Using a 3M transfer adhesive 1524, adhesive may be transferred from its original form to the protective shield by using a pressure nip set at approximately 100 psi. Following the pressure nip, release paper is removed and the material may be spooled upon itself to assume the form shown in FIG. 4. The adhesive is preferably slightly narrower than the protective shield and continuous along the length of the shield.

One further improvement of the present invention is to construct the protective shield from a material having a contrasting color so as to stand out from the other casting materials. For example, the protective shield may be constructed from blue, red, black, or other unique colored fibers so as to be easily distinguished from conventional white or off-white cast padding materials. Generally this will entail making the cast removal aid in a dark color, such as royal blue or black, that will distinctly contrast from the normally light color cast padding materials. In this manner, the casting technician can readily distinguish the exact location of the cast removal aid of the present invention and more easily cut along the cast removal aid during cast removal.

Alternative embodiments of the present invention may include different fiber types in conjunction with different weave patterns. For instance, a high modulus fiber, such as KEVLAR® or SPECTRA®, may be used in a particular denier and weave pattern that may provide cast saw protection. In contrast, a low modulus fiber, such as spandex, may likewise be used by providing a different denier and/or weave pattern that may also provide cast saw protection. Some forms of a removal strip may be in a tape form and be comprised of resistant materials like ceramics, composites, or metals. These tapes may be continuous or non-woven or in the form of a woven pattern. These tapes may be made from polyester, polypropylene, polyethylene or polyimides. Metal foil or braid tapes may also work in this application. For example, aluminum or copper in a foil tape form may resist a cast saw blade.

Figure 5:
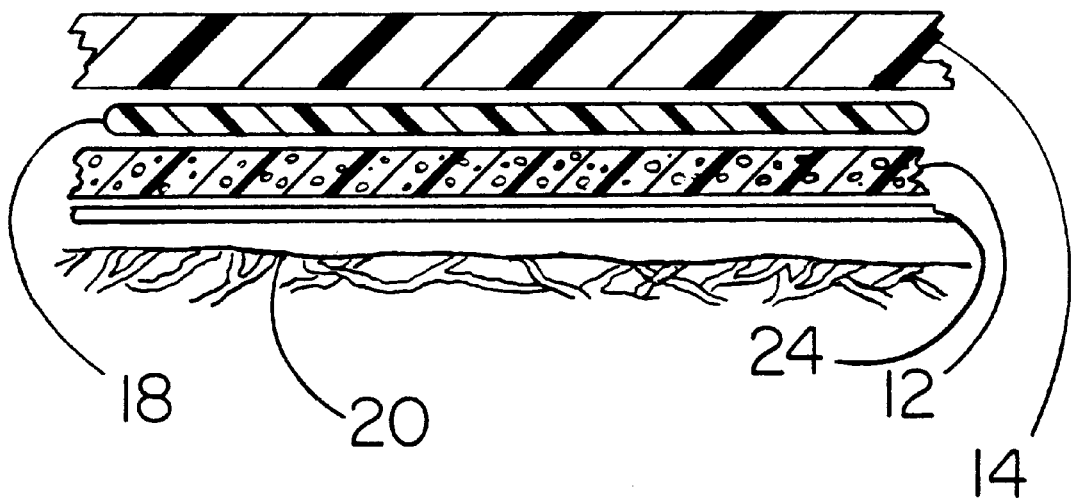
FIG. 5 is an enlarged longitudinal cross-section view of a conventional cast incorporating a protective shield of the present invention.

It should be appreciated that the protective shield of the present invention may be mounted in a wide variety of manner without departing from the present invention. For example, FIG. 5 illustrates mounting the protective shield 18 between the outer shell 14 and the cast padding 12. In this instance a stockinet 24 is also employed within the cast against the patient's skin.

Figure 6:
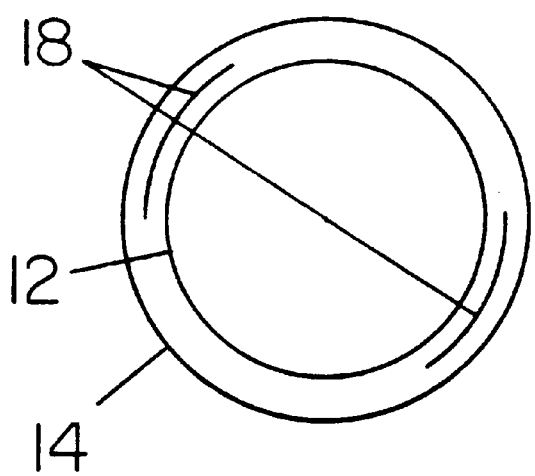
FIG. 6 is a transverse cross-section view of a cast illustrating the positioning of one embodiment of the protective shield of the present invention comprising multiple separate strips of protective shield.
Figure 7:
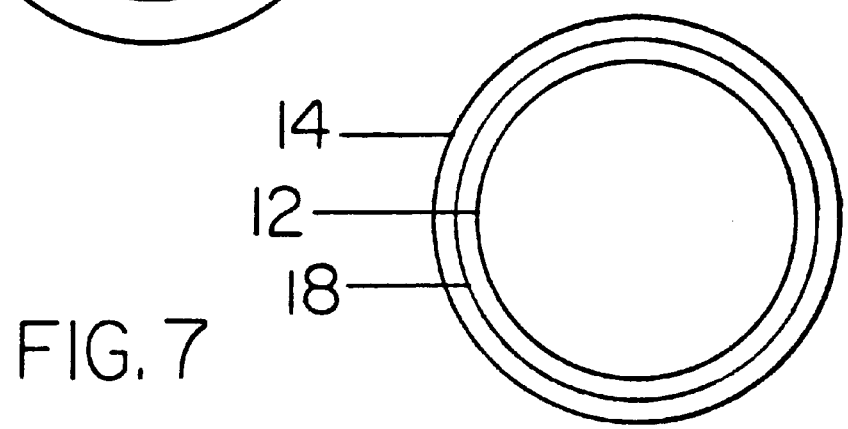
FIG. 7 is a transverse cross-section of a cast illustrating the positioning of another embodiment of the protective shield of the present invention comprising a single continuous cover of the protective shield.

The mounting technique illustrated in FIG. 5 may be accomplished as one or more separate strips of material, such as is shown in FIG. 6, or as a more extensive covering, such as is shown in FIG. 7.

Other possible orientations for the cast removal aid of the present invention include: (1) between the cast padding and the casting tape (i.e., outer shell material), applied in strips or continuously; (2) between the skin and the cast padding, applied in strips or continuously; (3) between a stockinet and the skin, applied in strips or continuously; (4) attached to the stockinet in strips or continuously; (5) attached to the cast padding so that the cast removal aid is applied as the padding is applied; and (6) attached to the casting tape itself. The protective shield of the present invention can also be employed in casts where little or no padding is used, such as in "total contact casting," as that employed with a "swimmer's cast" or in club feet casts.

From the foregoing description it should be understood that the protective shield of the present invention can be applied in any of the following ways: in strips covering only a portion of the area that is cast (with or without an adhesive attached to it); as a complete coverage; attached to the padding thus covering all areas the padding covers (in as many layers as the padding covers); attached to the stockinet (covering all areas the stockinet covers); attached to the casting tape (covering all areas covered by the casting tape); in replacement of the stockinet; integrated into the stockinet; integrated into the cast padding; or integrated into the casting tape.

The protective shield of the present invention can be applied in any type of cast including but not limited to: short arm casts; short leg casts; hip spica casts; thumb spica casts; short leg walker casts; body casts; gauntlet casts; long leg casts; etc.

The present invention may be employed with any type of casting material. The use of the phrase "casting tape" refers to any one of the synthetic casting tapes (fiberglass, etc.), plaster of paris bandages, any of the sleeve-like materials such as Quik Cast® or one of the more open structured materials, such as Hexalite® or X-Lite™ Orthopaedic Bandages. The use of the phrase "stockinet" refers to any one of the synthetic stockinets, cotton stockinets, or PANTALOON® Protective Liners.

Without intending to limit the scope of the present invention, the following examples illustrate how the present invention may be made and used:

EXAMPLE 1

A cast removal aid of the present invention may be made and tested in the following manner. Commercially available expanded PTFE fibers are acquired from W. L. Gore & Associates, Inc., Elkton, Md., under the trademark GORE-TEX®. The fibers comprise the following properties: a denier of about 1100 for both the warp and fill fibers, each having a generally rectangular cross-section; a tenacity at max of about 3.6 g/denier; an elongation to yield of about 2.7%; an elongation to break of about 21%; and a modulus of about 190 g/denier.

Figure 8:
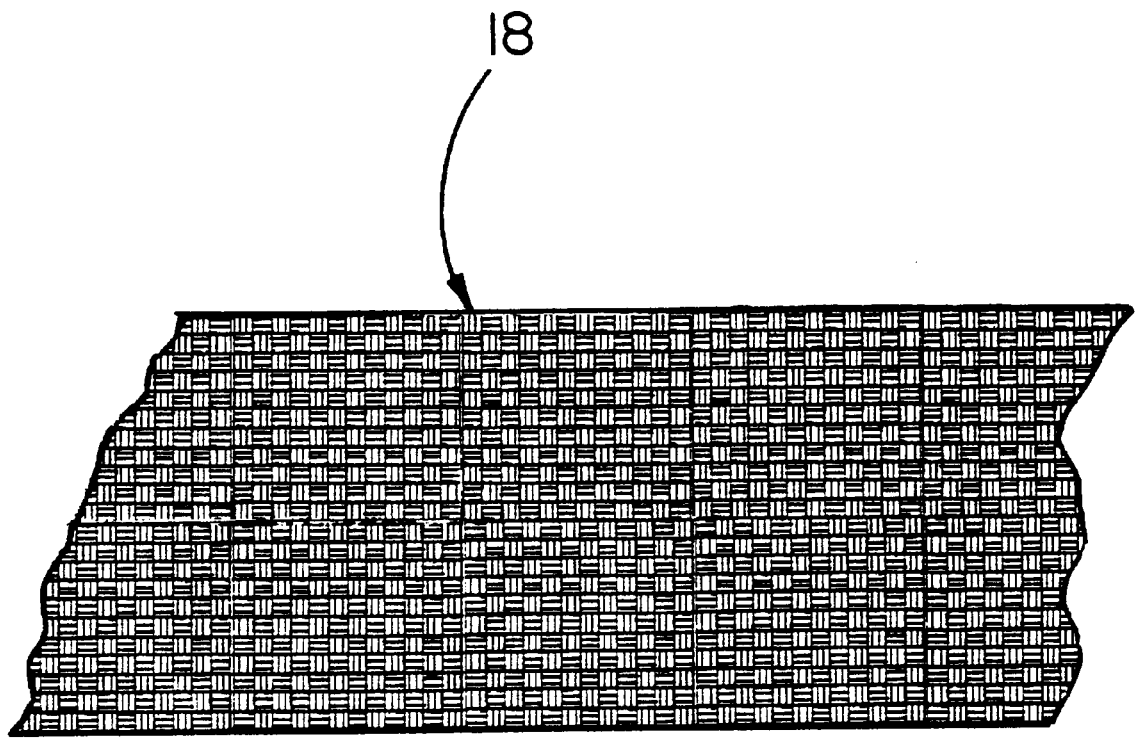
FIG. 8 is an enlarged plan view of a woven cast removal aid of the present invention made in accordance with Example 1.

The fibers are woven into a strip using a needle loom and twister, such as that commercially accessible from Bally Ribbon Mills in Bally, Pa. The needle loom setting is approximately 32 pics per inch and the weave has a warp of about 5 twists per inch. The final product comprises a strip having a width of approximately 3.2 cm and a thickness of about approximately 1 mm. The final woven pattern of the cast removal aid 18 is shown in FIG. 8.

The stripping is married to a medical grade transfer adhesive No. 1524 from 3M. The laminating process is done through a cold pressure nip. The nip is comprised of one roller being chrome steel and the other roller being silicone rubber with a durometer of 40. The nip has a pressure of approximately 100 psi. The release paper is removed from the adhesive following the nip and the strip is rolled into a roll. For a 3.2 cm wide strap, the adhesive was placed approximately 0.2 to 0.5 cm from each edge.

EXAMPLE 2

The cast removal aid made in accordance with Example 1 is tested in the following manner.

Three tests are believed important: cut resistance; moisture absorption; and skin compatibility. Material selection for all components is done based on these criteria. Prototypes are placed in mock casts on human subjects and removed by different individuals with varying technique. The varying techniques are graded in terms of visual perception of the pressure exerted on the cast by the cast saw and respective operator. Very poor technique translates into extreme pressure that would have cut through any fiberglass and padding and into a patient's arm causing a burn or cut. Great technique translates into very light pressure in an up and down motion that selectively cut through only the fiberglass and not the padding.

For most of the cut resistance tests, the protective shields are approximately 3 cm wide and located between two layers of GORES® Cast Liner padding and a fiberglass outer shell comprising three layers of 3 inch Johnson & Johnson DELTA-LITE® Conformable Casting Tape. The protective shields are removed following cast saw contact over a length approximate to a short arm cast. The shields are removed and inspected for damage. Damage is graded into three categories: (1) compromised protective shield with damaged padding beneath; (2) compromised fibers in the shield with no damage to padding; and (3) scarring of the shield with no fibers compromised and with no damage to padding.

A protective shield made in accordance with Example 1 was tested for cut through resistance under these criteria with a Zimmer® Cast Cutter II oscillating cast removal saw, Model No. 8908-01, manufactured by Zimmer of Warsaw, Ind. The protective shield made in accordance with Example 1 consistently achieved a Category 3 performance, even under poor cast removal techniques.

Given that the protective shield of the present invention may be used with water resistant casts, it is desirable for the moisture absorption characteristics of the material to be low. To this end prototypes are weighed dry and then submerged in a 0.5% liquid soap by volume solution for 5 minutes. The prototypes are removed and allowed to drip for 15–20 seconds and then weighed again. The second weight is divided by the first weight to establish a ratio followed by the subtraction of 1 to produce a percentage of moisture retention. Values of the protective shield made in accordance with Example 1 were less than 15% moisture retention using the described test method.

Finally, since the protective shield may be placed in a cast in close proximity to a patient's skin, it is important to ensure intimate skin compatibility by accepted industry standards. Biological Test Center in Irvine, Calif., was used to determine skin compatibility on prototypes. Three tests were conducted: USP Intracutaneous Reactivity (Normal Saline and Oil); CFR Primary Skin Irritation; and GP Maximization Sensitization. The protective shield made in accordance with Example 1 scored a "weak" in each of these categories, indicating that it is quite bio-compatible. This demonstrates that the protective shield is suitable for direct skin contact.

While particular embodiments of the present invention have been illustrated and described herein, the present invention should not be limited to such illustrations and descriptions. It should be apparent that changes and modifications may be incorporated and embodied as part of the present invention within the scope of the following claims.

The invention claimed is:

1. A cast comprising
   an outer shell;
   a cast removal aid positioned between the outer shell and a patient's skin, the cast removal aid comprising a protective shield of material that is resistant to cut-through by cast removal tools; and
   wherein the cast removal aid comprises expanded polytetrafluoroethylene fibers.

2. The cast of claim 1 wherein the cast removal aid comprises a strip of material.

3. The cast of claim 2 wherein
   the cast includes a cast padding comprising a first color; and
   the cast removal aid comprises a color that is contrasting from and easily distinguished from the color of the cast padding.

4. The cast of claim 1 wherein the cast further includes a cast padding.

5. The cast of claim 4 wherein the cast removal aid is positioned between the outer shell and the cast padding.

6. The cast of claim 1 wherein the cast removal aid comprises a woven strip of expanded polytetrafluoroethylene fibers.

7. The cast of claim 6 wherein the strip is constructed of expanded polytetrafluoroethylene fibers having a weight of between about 400 and about 1600 denier.

8. The cast of claim 6 wherein the strip includes an adhesive to hold the strip in place during the casting procedure.

9. A cast removal aid comprising:
   protective shield material, the material comprising woven fibers that are resistant to cut-through by cast removal tools when mounted beneath an outer shell of a cast;
   the woven fibers providing conformability to the cast removal aid so as to allow the cast removal aid to be formed directly within the cast.

10. The cast removal aid of claim 9 wherein the protective shield material comprises a weave including expanded polytetrafluoroethylene fibers.

11. The cast removal aid of claim 10 wherein the woven expanded polytetrafluoroethylene fibers comprise a weight of between about 400 and 1600 denier.

12. The cast removal aid of claim 9 wherein the cast removal aid includes an adhesive to assist in positioning the cast removal aid during casting.

13. The cast removal aid of claim 9 wherein the protective shield material comprises a dark color.

* * * * *